United States Patent [19]
Hertel

[11] Patent Number: 6,009,887
[45] Date of Patent: Jan. 4, 2000

[54] ADJUSTABLE LIQUID/GEL APPLICATOR

[76] Inventor: Sandra Hertel, 234 S. Benjamin, Stillwater, Okla. 74074

[21] Appl. No.: 09/314,720

[22] Filed: May 18, 1999

Related U.S. Application Data

[60] Provisional application No. 60/086,044, May 19, 1998.

[51] Int. Cl.⁷ .................................................. A45D 40/24
[52] U.S. Cl. ...................... 132/317; 132/320; 15/104.94; 15/244.2; 15/144.2; 401/6
[58] Field of Search .................................. 132/317, 286, 132/320, 218; 15/104.94, 244.1, 244.2, 144.1, 144.2; 401/6

[56] References Cited

U.S. PATENT DOCUMENTS

| | | | |
|---|---|---|---|
| 2,829,393 | 4/1958 | Turcotte | 15/131 |
| 3,362,037 | 1/1968 | Griffin | 15/144.1 |
| 3,704,480 | 12/1972 | Whitaker | 15/144.2 |
| 4,148,318 | 4/1979 | Meyer | 128/269 |
| 4,225,254 | 9/1980 | Holberg et al. | 401/119 |
| 4,299,005 | 11/1981 | Brown | 15/244.2 |
| 4,308,879 | 1/1982 | Thornbloom | 132/88.5 |
| 4,455,705 | 6/1984 | Graham | 15/121 |
| 4,483,356 | 11/1984 | Kales | 132/88.7 |
| 4,609,301 | 9/1986 | Benarrouch | 401/196 |
| 4,618,279 | 10/1986 | Gurevich et al. | 401/36 |
| 4,658,461 | 4/1987 | Roe et al. | 15/144.1 |
| 4,747,720 | 5/1988 | Bellehumeur et al. | 401/205 |
| 4,925,327 | 5/1990 | Wirt | 401/205 |
| 4,927,283 | 5/1990 | Fitjer | 401/132 |
| 4,936,700 | 6/1990 | Morris | 401/196 |
| 5,088,849 | 2/1992 | Johnson et al. | 401/44 |
| 5,125,757 | 6/1992 | Morrison et al. | 401/21 |
| 5,299,877 | 4/1994 | Birden | 401/206 |
| 5,509,744 | 4/1996 | Frazier | 401/132 |
| 5,566,418 | 10/1996 | Steffen et al. | 15/244 |
| 5,581,838 | 12/1996 | Rocco | 15/144.1 |
| 5,615,962 | 4/1997 | Staub | 401/173 |
| 5,659,916 | 8/1997 | Beatty et al. | 15/144.1 |

*Primary Examiner*—Gene Mancene
*Assistant Examiner*—Pedro Philogene
*Attorney, Agent, or Firm*—Head, Johnson & Kachigian

[57] ABSTRACT

An applicator for applying fluid, liquid, gel, medicine or lotion to the human body. The applicator has a handle, an applicator head and a pivot lock. The pivot lock positions the applicator head at a number of discrete positions with respect to the handle. The applicator head has a clevis with a first fork and a second fork. The first fork and the second fork have star-shaped openings. The handle has a base with a star-shaped aperture. A star-shaped extrusion on the pivot lock fits through the star-shaped openings and the star-shaped aperture to lock the position of the applicator with respect to the handle. The pivot lock also has a spring rod with a spring a compression spring around it. The spring is compressed between a shoulder and a spring rod cap. The spring rod fits into a spring rod opening in a structural member between the clevis and a dispenser portion of the applicator head. When the spring rod is placed through the spring rod opening, the spring is placed around the pivot and compressed against an annular shoulder of the applicator head. A pivot cap is then placed on the pivot to retain the spring. The spring is a compression spring which pushes on the end of the pivot cap to bias a base of the pivot lock against an outer face of a first fork of the clevis. Pulling the pivot base disengages the star-shaped extrusion from the star-shaped aperture, causing the applicator head to be pivotable about a cylindrical pivot.

20 Claims, 2 Drawing Sheets

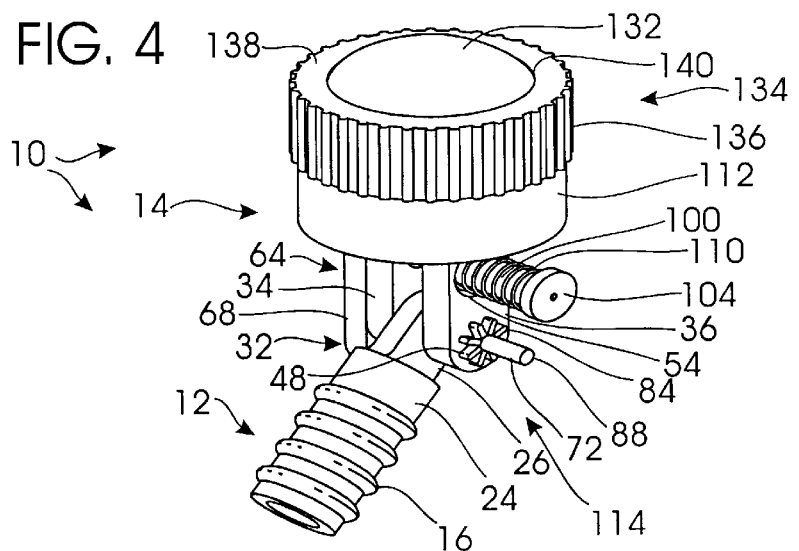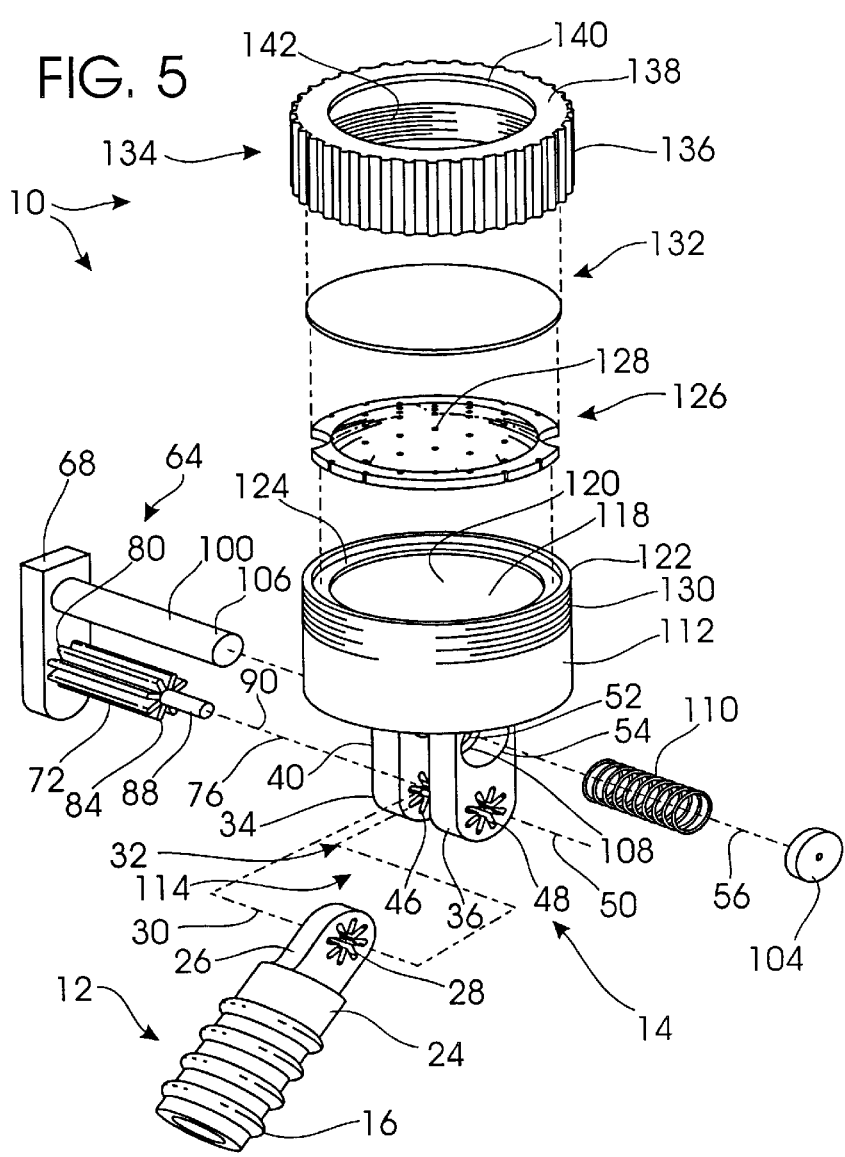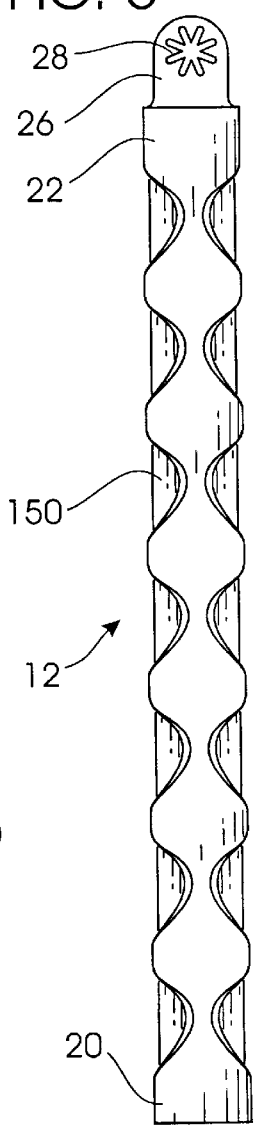

ADJUSTABLE LIQUID/GEL APPLICATOR

CROSS-REFERENCE OF RELATED APPLICATION

This application claims priority to U.S. Provisional Application No. 60/086,044, filed May 19, 1998.

BACKGROUND OF THE INVENTION

1. Field of the Invention

The present invention is for an applicator to apply fluid, liquid, gel, medicine or lotion to a human or animal body. In particular, the invention is for an applicator having interchangeable heads that may be adjustably positioned.

2. Background of the Invention

An applicator may be used to apply fluid, cream, gel, medicine or lotion (collectively referred to as lotion in this specification) to hard-to-reach places, such as a person's back. A lotion applicator may also be used to avoid contaminating the lotion by the hands and to avoid getting lotion on the hands. The lotion applicator may also be useful for people with disabilities who may have difficulty in reaching parts of their body which people of normal abilities can easily reach. The lotion applicator may also be used for applying lotion to animals.

There have been several applicators in the past. For example, Turcotte (U.S. Pat. No. 2,829,393) discloses a dispenser having a frame with a hollow concave bottom surface to receive lotion. A porous pad stretched over a frame handle may be unscrewed to saturate the porous pad with lotion.

Meyer (U.S. Pat. No. 4,148,318) discloses a tool with a handle having a reservoir separated from a sponge by plastic or metal. The plastic or metal is pierced by sharpened rods to release solution.

Holberg et al. (U.S. Pat. No. 4,425,254) discloses a surgical scrub device having a hollow handle for storage of liquid and a replaceable sponge retained on dispensing tip by detent protrusions.

Wirt (U.S. Pat. No. 4,925,327) discloses a liquid applicator with an inner layer of porous metering material and an outer layer of open-cell foam sponge material to regulate the flow of liquid.

Staub (U.S. Pat. No. 5,615,962) discloses lotion applicator with a one-piece frame, an elongated handle, a reservoir, and an applicator.

Although there have been several applicators in the past, there remains a need for an applicator that can lock an applying surface at several, discrete positions. The applying surface must be capable of being moved over an area of skin while overcoming frictional resistance without changing the position of the applying surface with respect to the handle.

There additionally remains a need for an applicator with interchangeable heads that may be quickly and easily interchanged.

SUMMARY OF THE INVENTION

The present invention is for an applicator to apply liquid or gel to human or animal skin. The applicator has a handle attached to an applicator head. The applicator head has a sponge pad to apply the lotion. The handle allows the person to position the sponge pad at hard-to-reach locations on the body. The person applies lotion by moving the handle such that the sponge pad is rubbed over the areas of the body requiring lotion.

Some of the applicators used in the past have had a handle with an applicator head fixed at one given angular position with respect to the handle. This physical arrangement makes it difficult for a user to keep the applicator sponge pad parallel to various curvatures of the body. In turn, the lotion is not evenly distributed and parts of the applicator head other than the pad rub against the body.

Other lotion applicators used in the past have permitted the applicator head to swivel with respect to the handle. Allowing the sponge pad to swivel positions the applicator pad parallel to the body at various body contours. However, locking the applicator pad at different positions with respect to the handle gives the user more control in positioning the applicator pad. Because the user has more control of the position of the applicator pad, the applicator is easier to use and the user is less likely to contaminate clothing or other items.

In the present invention, the applicator has a pivot lock to lock an applicator head, and in turn an applicator pad, at different angular positions with respect to the handle. The handle is of sufficient length to allow the user to position the applicator pad at hard-to-reach places on the user's body.

The applicator head consists of at least two basic designs: (a) an applicator head with a pad, a reservoir for lotion in the applicator head, and a device for dispensing the lotion; and (b) an applicator head with a pad, for which a person puts lotion on an outside surface of the pad to apply the lotion to the body.

The applicator is preferably made of a lightweight material and not subject to rust or corrosion, such as plastic, metal, hardwood, stainless steel, rubber or aluminum.

One object of the invention is to provide an applicator of lotion which applies lotion evenly to hard-to-reach areas of the body.

Another object of the invention is to provide a pivot lock which locks the applicator head in several discrete positions with respect to the applicator handle.

Yet another object of the invention is to provide an applicator which is durable and not easily broken.

A still further object of the invention is to provide an applicator which is easy to use for people with disabilities and easy to use on animals.

Still another object of the invention is to provide an applicator that will minimize contamination when used on humans or animals.

Another object of the invention is to provide an applicator that will minimize the waste of lotion.

BRIEF DESCRIPTION OF THE DRAWINGS

FIG. 4 is a partial perspective view of the applicator of the present invention.

FIG. 5 is a partial, exploded perspective view of the applicator of the present invention.

FIG. 6 is a side view of a handle of the applicator of the present invention.

DETAILED DESCRIPTION OF THE PREFERRED EMBODIMENTS

Figure 1:
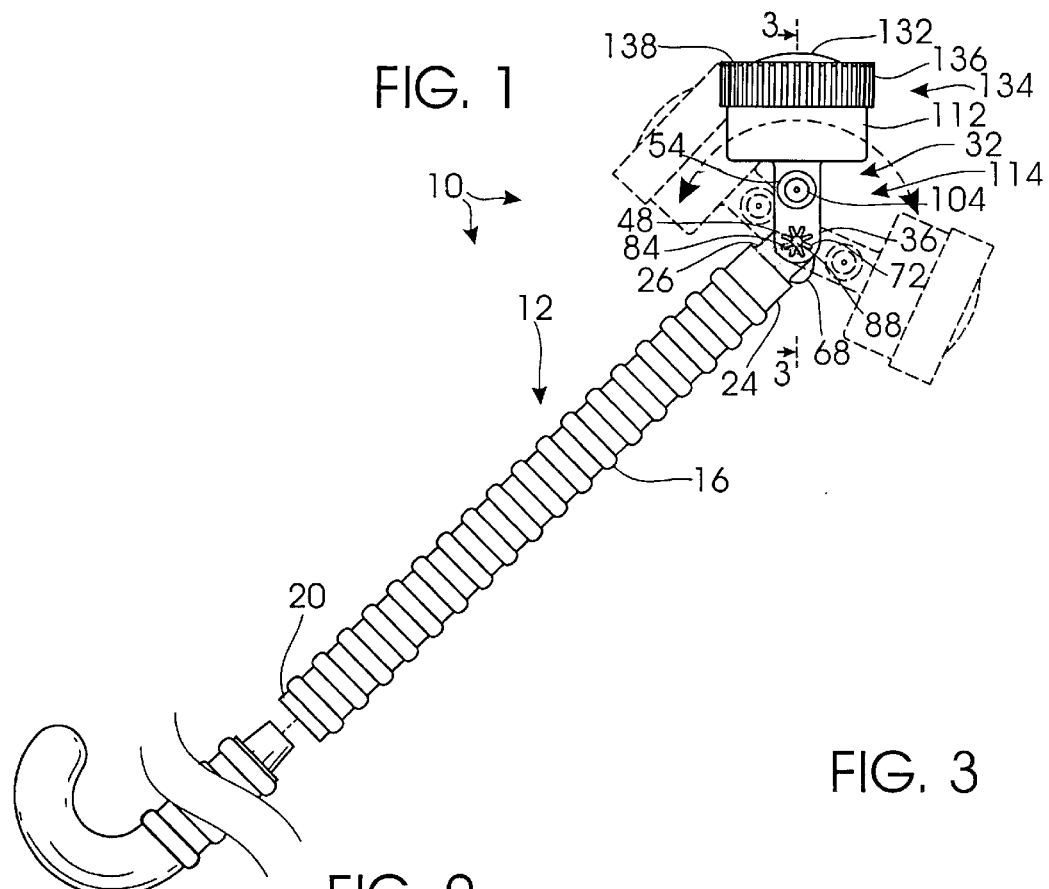
FIG. 1 is a side view of an applicator constructed in accordance with the present invention, showing alternate positioning of an applicator head.
Figure 2:
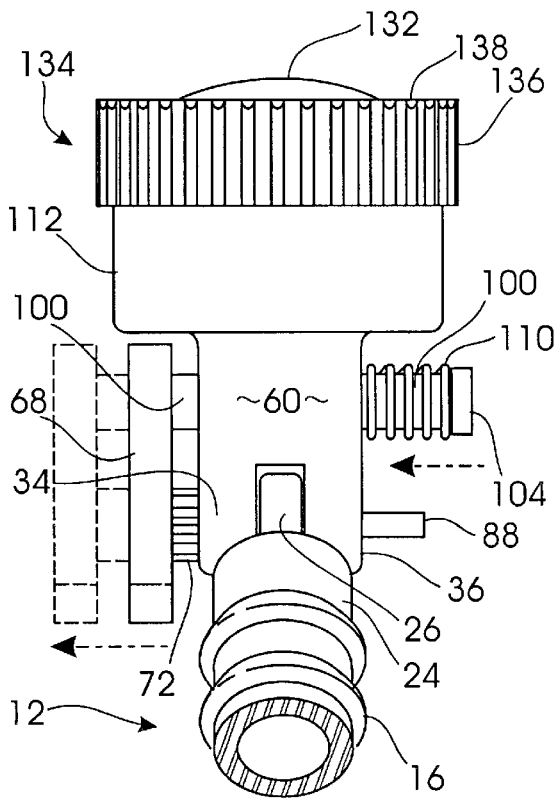
FIG. 2 is a partial, front view of the applicator shown in FIG. 1 constructed in accordance with the present invention.

Like part numbers in the various drawings indicate like parts in the invention. Referring to the drawings in detail, FIGS. 1 through 5 show different views and different components of a single preferred embodiment of the invention.

In FIGS. 1 through 5, an applicator 10 has a handle 12 and an applicator head pivotally attached to the handle 12. The handle 12 has knurls 16 to aid a user in grasping the handle 12. The handle 12 has a first end 22 and a second end 24. The handle second end 24 has a base 26 with a generally star-shaped aperture 28. As shown in FIG. 1, the aperture 28 is not a true star shape but is referred to as star-shaped in this specification. The aperture 28 has a centerline 30.

The applicator head 14 has a clevis 32 with a first fork 34 and a second fork 36. The first fork 34 has an outer face 40. The first fork 34 has a first fork opening 46 that is the same size and shape as the star-shaped aperture 28. The second fork 36 has a second fork opening 48 the same size and shape as: (a) the star-shaped aperture 28, and (b) the first fork opening 46. The first fork opening 46 opposes the second fork opening 48. The first fork opening 46 and the second fork opening 48 share a common centerline 50. A circle is inscribed at a center of the star shape.

The applicator head 14 also has a structural member 60 extending between clevis 32 and dispenser 112. A rod opening 52 passes approximately halfway through structural member 60 and widens to a larger spring opening 54. The spring opening 54 is concentric to the rod opening 52. The rod opening 52 and the spring opening 54 have a common centerline 56.

As best seen in FIG. 5, pivot lock 64 has a star-shaped extrusion 72 and a cylindrical rod 82 fixed to a pivot lock base 68. The star-shaped extrusion 72 has a first end 80 attached to the pivot lock base 68 and a second end 84. A pivot 88 extends from the extrusion second end 84. Cylindrical rod 100 is smaller than rod opening 52, so that the rod 100 can freely pass through rod opening 52. Star-shaped extrusion 72 is slightly smaller, but of the same shape, as the star-shaped aperture 28 in base 26. As mentioned above, the star-shaped aperture 28 is the same size and shape as the first fork opening 46 and the second fork opening 48. Thus, the precise size and shape of star-shaped extrusion 72 are selected so that star-shaped extrusion 72 passes freely through first fork opening 46, star-shaped aperture 28, and second fork opening 48.

When in place, the star-shaped extrusion 72 shares a centerline 76 with the centerline 50 common with the aperture 28, the first fork opening 46, and the second fork opening 48. The rod 100 has a centerline 102. The distance between the star-shaped extrusion centerline 76 and the spring rod centerline 102 is the same as the distance between star-shaped aperture centerline 30 and the rod opening centerline 52. This allows rod 100 to fit into rod opening 52 while the star-shaped extrusion 72 fits into the first fork opening 46, the aperture 28 and the second fork opening 48.

As best seen in FIG. 5, there is an annular shoulder 108 extending from a wall of the rod opening 52 to a wall of the spring opening 54. This annular face 108 is perpendicular to rod opening centerline 56 and is located in the interior of structural member 60 at a plane where rod opening 52 widens to spring opening 54.

The applicator head 14 is attached to handle 12 by simultaneously sliding: (a) the star-shaped extrusion 72 into the first fork opening 46 and (b) the spring rod 100 into pivot opening 52. While cylindrical pivot 100 passes through rod opening 52 and spring opening 54, star-shaped extrusion 72 passes successively through first fork opening 46, star-shaped aperture 28 of handle base 26, and finally through second fork opening 48. The sliding stops and the pivot lock 64 is in the locked position when the pivot lock base 68 abuts the first fork outer face 40.

In assembling the applicator 10, with the pivot lock 64 in the locked position, compression spring 110 is slipped over the exposed end 106 of the spring rod 100. When no external forces act on the spring 110, the spring 110 is normally longer than an exposed length of rod 100, which is the distance between the annular shoulder 108 and the rod end 106, when the pivot lock 64 is in the locked position. Spring 110 is compressed until a length of the compression spring is less than distance from annular shoulder 108 to the rod end 106. Spring rod cap 104 is affixed to the spring rod end 106 to retain spring 110 on spring rod 100, with the spring 110 in a slightly compressed state.

In order to rotate the applicator head 14 to a new position, with respect to the handle 12, a user pulls the pivot lock base 68 until the extrusion 72 is disengaged from star-shaped aperture 28. When the user pulls the pivot lock base 68 the spring 110 is compressed. The user slightly rotates the pivot lock base 68, and in turn the applicator head 14, about pivot 88 until the extrusion second end 84 is abutting the handle base 26. The user may then stop pulling on the pivot lock base 68. The user continues to rotate the pivot lock base 68 until the star-shape extrusion 72 aligns with the star-shaped aperture 28. When the star-shaped extrusion 72 aligns with the star-shaped aperture 28, the compression spring 110 pushes on cap 104, which pulls the star-shaped extrusion 72 through the star-shaped aperture 28 and into the second fork opening 48. When the pivot lock base 68 abuts the first fork outer face 40, the pivot lock 64 is again in the locked position.

Figure 3:
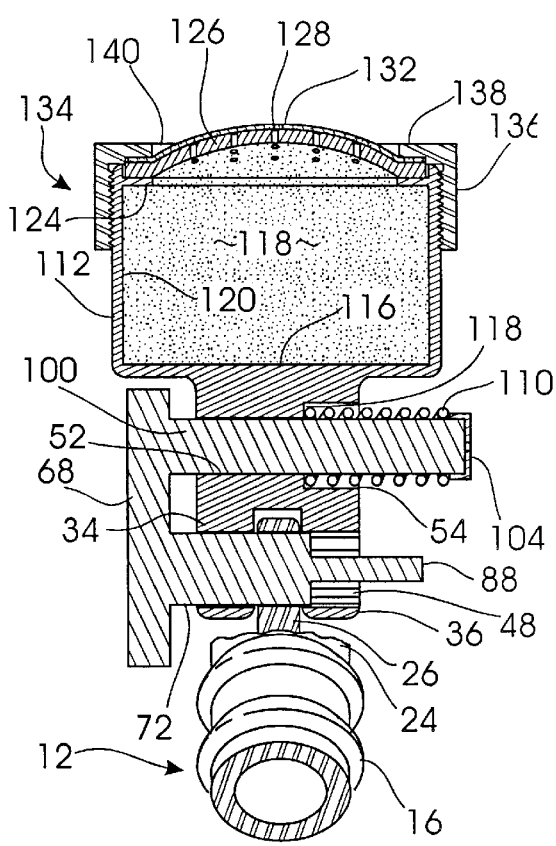
FIG. 3 is a partial sectional view of an applicator of the present invention.

As best seen in FIGS. 3 and 6, the applicator head 14 has a cylindrical dispenser 112 attached to the structural member 60. The cylindrical dispenser 112 has a bottom 116 forming a reservoir 118 with a cylindrical wall 120. The reservoir 118 holds the lotion that is to be dispensed. The lotion is dispensed at the top 122 of the cylindrical dispenser 112.

At the dispenser top 122, there is an annular lip 124 attached to the dispenser cylindrical wall 120. There are external dispenser threads 130 near dispenser top 122. A medicine gauge 126 rests on top of the annular lip 124. The medicine gauge 126 has a plurality of holes 128 in it to regulate the flow rate of lotion. The number and size of holes 128 will depend on the physical properties, such as viscosity and density, of the lotion being dispensed. The medicine gauge 126 is interchangeable with medicine gauges having different numbers of holes and different hole sizes.

An absorbent pad 132, such as a sponge, abuts the medicine gauge 126. The pad 132 is approximately the same size in diameter as the medicine gauge 126. The diameters of the pad 132 and the medicine gauge 126 are: (a) greater than an inner diameter of the annular lip 124, and (2) less than a diameter of the dispenser cylindrical wall 120. The absorbent pad 132 absorbs fluid from the reservoir 118 which then spreads through the pad 132 by capillary action. The absorbent pad 132 assists in even distribution of the lotion from the dispenser 112.

The dispenser top 122 is partially covered by a lid 134, having a side portion 136 and a top portion 138. The lid side portion 136 has internal threads 142 which screw onto the dispenser threads 130, holding the lid 134 in place on the dispenser 112. The lid top portion 138, which has a lid top opening 140, covers the outer edges of pad 132, the medicine gauge 126 and the annular lip 124.

In FIG. 6, handle 12 has finger grips 150 to facilitate gripping of the handle by a user.

The applicator may be made of materials not subject to corrosion, such as plastic, hardwood, stainless steel, rubber or aluminum.

While the invention has primarily been described as a self-applicator for human use, it will be understood that the device may also be used as an applicator for applying medicine or lotions to animals.

Whereas, the present invention has been described in relation to the drawings attached hereto, it should be understood that other and further modifications, apart from those shown or suggested herein, may be made within the spirit and scope of this invention.

What is claimed is:

1. An applicator to apply gel or fluid, comprising:
   (a) a handle which may be grasped;
   (b) a handle base extending from said handle, said base having a shaped aperture;
   (c) an applicator head pivotally connected to said handle, said applicator head including a dispenser for said gel or fluid and a spring rod opening;
   (d) a pivot lock having an extending spring rod and an extrusion shaped to mate with said aperture; and
   (e) a spring retained over said spring rod, wherein said pivot lock extrusion locks said applicator head to said handle in a position, and wherein pulling a pivot base of said pivot lock disengages said shaped extrusion from said aperture, allowing said applicator head to pivot with respect to said handle.

2. The applicator of claim 1 wherein said applicator is made of plastic.

3. The applicator of claim 1 wherein said applicator is made of rubber.

4. The applicator of claim 1 wherein said applicator is made of hardwood.

5. The applicator of claim 1 wherein said applicator is made of stainless steel.

6. The applicator of claim 1 wherein said applicator is made of aluminum.

7. An applicator to apply gel or fluid, comprising:
   (a) a handle which may be grasped having a base extending from the handle; and
   (b) at least one applicator head, each said applicator head having a pivot and lock mechanism, said pivot and lock mechanism having an extending spring rod and an extrusion shaped to mate with an aperture on said base, so that said at least one applicator head may be interchangeably connected to said handle.

8. An applicator for a user to apply gel or fluid to a human or animal body, comprising:
   (a) a handle which the user can manually grasp and move;
   (b) a handle base with a star-shaped aperture;
   (c) an applicator head pivotally connected to the handle;
   (d) a clevis attached to said applicator head having a first fork and a second fork, wherein said first fork has a first fork opening and said second fork has a second fork opening;
   (e) a cylindrical dispenser for dispensing lotion, forming a part of said applicator head;
   (f) a structural member extending between said clevis and said dispenser, said structural member having a spring opening and a spring rod opening, said spring opening and said spring rod opening sharing a common centerline;
   (g) a pivot lock with a pivot lock base rigidly attached to a spring rod and a first end of a star-shaped extrusion;
   (h) a cylindrical pivot extending from a second end of said extrusion;
   (i) a compression spring positioned around said spring rod;
   (j) a spring rod cap attached to an end of said spring rod;
   (k) a shoulder in said structural member, said compression spring extending between said shoulder and said spring rod cap to bias said pivot lock base against a first fork outer face;
   (l) wherein said fork extrusion fits into said first star-shaped opening, said star-shaped aperture and said second fork opening to lock the position of the applicator head with respect to said handle; and
   (m) wherein pulling said pivot lock base to depress the compression spring between the cap and said shoulder disengages the star-shaped extrusion from said star-shaped aperture, causing said applicator head to be pivotable about said cylindrical pivot.

9. The lotion applicator of claim 8 wherein said dispenser further comprises:
   (n) an annular lip about a top of said dispenser, said dispenser forming a reservoir for storage of said lotion;
   (o) an applicator pad to receive lotion from said reservoir and apply it to the human or animal body, said applicator pad on top of said lip; and
   (p) a lid with a top having an opening, said lid top retaining said applicator pad by compressing said pad against said lip.

10. The lotion applicator of claim 9 wherein said applicator head further comprises:
    (q) external dispenser wall threads positioned on a cylindrical outer wall of said dispenser; and
    (r) lid internal threads engageable with said external dispenser wall threads, wherein turning said lid internal threads against said external dispenser wall threads causes said lid to compress said applicator pad between said lip and a top portion of said lid.

11. The lotion applicator of claim 9 wherein said applicator head further comprises a medicine gauge having holes therethrough, said medicine gauge located between said applicator pad and said reservoir, to control the flow of lotion from said reservoir to said applicator pad.

12. The lotion applicator of claim 8 wherein said handle has finger grips to facilitate gripping of said handle by the user.

13. An applicator to apply gel or fluid, comprising:
    (a) a handle which may be grasped; and
    (b) an applicator head pivotally attached to said handle by a pivot lock, wherein said applicator head is rotatable about a cylindrical pivot when a shaped extrusion of said pivot lock is disengaged from a shaped aperture in a base of said handle.

14. The applicator of claim 13 wherein said applicator head includes a dispenser for dispensing the gel or the fluid.

15. The applicator of claim 13 further comprising a medicine gauge to control the flow of lotion from the dispenser.

16. The applicator of claim 13 wherein said applicator is made of plastic.

17. The applicator of claim 13 wherein said applicator is made of rubber.

18. The applicator of claim 13 wherein said applicator is made of stainless steel.

19. The applicator of claim 13 wherein said applicator is made of aluminum.

20. The applicator of claim 13 wherein said applicator is made of hardwood.

* * * * *